United States Patent [19]

Fiedler

[11] 4,234,477

[45] Nov. 18, 1980

[54] α-N-ACETYL-L-PHENYLALANYL-L-ARGININE ETHYL ESTER

[75] Inventor: Franz Fiedler, Munich, Fed. Rep. of Germany

[73] Assignee: Bayer Aktiengesellschaft, Leverkusen, Fed. Rep. of Germany

[21] Appl. No.: 18,702

[22] Filed: Mar. 8, 1979

[30] Foreign Application Priority Data

Mar. 30, 1978 [DE] Fed. Rep. of Germany ....... 2813772

[51] Int. Cl.³ .................... C07C 103/52; C12Q 1/36
[52] U.S. Cl. ................................ 260/112.5 R; 435/24
[58] Field of Search .................... 260/112.5 R; 435/24

[56] References Cited

PUBLICATIONS

Pettit, "Synthetic Peptides," vol. 3, (1978).

T. Morita, "Computer Print Out Mid-Line," J. Biochem. (Tokyo) 85 (2) 1495-1498, 1977.

Primary Examiner—Delbert R. Phillips
Attorney, Agent, or Firm—Sprung, Felfe, Horn, Lynch & Kramer

[57] ABSTRACT

The new compound acetylphenylalanyl-arginine ethyl ester (Ac-Phe-Arg OEt) and its acid addition salts are used in the diagnostic determination of the content of Kallikrein. In view of the role of Kallikrein in regulating blood pressure or the renal function, the reliable determination of small amounts of Kallikrein such as occur in urine, saliva or glands is important but has been difficult to achieve. Ac-Phe-Arg OEt and its esters provide a substrate for use in such determinations and allow a significant improvement in accuracy.

7 Claims, No Drawings

α-N-ACETYL-L-PHENYLALANYL-L-ARGININE ETHYL ESTER

The present invention relates to the new dipeptide derivative α-N-acetyl-L-phenylalanyl-L-arginine ethyl ester (abbreviated form: Ac-Phe-Arg OEt) and its acid addition salts, and their use as a substrate for Kallikrein ®, preferably for use in the diagnostic determination of the content of Kallikrein, especially of small amounts of Kallikrein, such as occur, for example, in urine, saliva or glands.

Because of the role of Kallikrein (EC No. 3.4.4.21) in regulating blood pressure or the renal function, the determination of Kallikrein in urine is diagnostically important.

Because of the low amounts of Kallikrein in urine, reliable determination of the content of Kallikrein is extremely difficult to carry out using the methods customary at present. The methods known hitherto have the following disadvantages: Z-Tyr p-nitrophenyl ester is a sensitive substrate for urine Kallikrein, but it is less sensitive than the compound according to the invention, and spontaneous hydrolysis takes place very rapidly.

Furthermore, D-valyl-leucyl-arginine p-nitroanilide (D-Val-Leu-Arg p-nitroanilide S 2266 KABI, Mölndal) was recently introduced as a substrate for Kallikrein from glands. However, the method of determination using the compounds according to the invention is 38 times more sensitive.

It is possible to determine urine Kallikrein by a very sensitive method with the aid of radioactively labelled Tos-Arg OMe (tosylarginine methyl ester=TAME) (Beaven et al; Clin. Chim. Acta 32, 67–73). However, this method requires very special and expensive equipment and calibration using a standard preparation of urine Kallikrein and does not permit continuous recording of the reaction.

In contrast, the sensitivity of the Kallikrein determination using Ac-Phe-Arg OEt as the substrate is sufficient by far to carry out a convenient and problem-free determination of the Kallikrein, for example in urine, saliva or glands.

According to the present invention we provide acetylphenylalanyl-arginine ethyl ester (Ac-Phe-Arg OEt) or an acid addition salt thereof, and a process for its production in which N-acetyl-L-phenylalanine is reacted with L-arginine ethyle ester, or an acid-addition salt thereof, e.g. its hydrochloride, in an organic solvent in the presence of trialkylamine, particularly one containing up to 12, preferably up to 6 and particularly 1 to 4 carbon atoms in each alkyl group, and a water-binding reagent and the reaction product is isolated. A preferred process is one in which N-acetyl-L-phenylalanine in dimethylformamide is reacted with L-arginine ethyl ester dihydrochloride in the presence of triethylamine and N-hydroxysuccinimide and the reaction product is isolated by chromatography on a crosslinked polydextran gel containing carboxymethyl groups and subsequent solution in ethanol and precipitation with ethyl acetate.

The enzyme Kallikrein belongs to the peptidylpeptide hydrolase group and, in contrast to most enzymes of this class, is distinguished by a high substrate specificity. By splitting two peptide bonds, it liberates the pharmacologically extremely active kinins only from the glycoprotein which occurs in the globulin fraction of serum and is called kininogen.

Kallikrein activity can be determined quantitatively with the aid of its hypotensive action on the test animal, by comparison with a standard preparation ("Pedutin" (Trade Mark) standardised Kallikrein from the pancreas of pigs) (E. K. Frey et al.: Das Kallikrein-Kinin-System und seine Inhibitoren (The Kallikrein/kinin system and its inhibitors), Enke-Verlag, Stuttgart 1968). However, this method is relatively inaccurate.

A further biological method for the determination of Kallikrein comprises the amount of kinin liberated per unit time, which can be determined, likewise in comparison with a standard kinin preparation, by measuring the contracting action on the uterus or intestine ( E. K. Frey et al.: Das Kallikrein-Kinin-System und seine Inhibitoren (The Kallikrein/kinin system and its inhibitors), Enke-Verlag Stuttgart 1968). As a biological method, this method is likewise relatively inaccurate and expensive.

Optical measurement of the activity with the aid of the ester-splitting action of Kallikrein is more simple and more exact than the two above-mentioned biological methods of determination.

Benzoyl-L-arginine ethyl ester (Bz-Arg OEt=BAEE) is preferably suitable as a substrate for measuring the esterolytic activity of Kallikrein. In this context see: Methoden der enzymatischen Analyse (Methods of enzymatic analysis), volume I, 1071–1080, Weinhein 1974. The principle of this method can be represented briefly as follows:

  (A)

  (B)

the abbreviations used in the above formulae having the following meaning:

| | | |
|---|---|---|
| Bz-Arg OEt | = | benzoylarginine ethyl ester |
| Bz-Arg | = | benzoylarginine |
| NAD⊕ | = | positively charged form of NAD (nicotinic acid amide-adenine dinucleotide) |
| ADH | = | alcohol dehydrogenase (from yeast) |
| NADH | = | reduced form of NAD (reduced in the pyridine part) |

The equilibrium of equation (A) lies far on the side of the cleavage products. The splitting of Bz-Arg OEt provides five possible ways for determining the activity. The most reliable and most simple is the enzymatic measurement, by a reaction coupled with the splitting reaction, of the amount of ethanol liberated (in this context see equation (B)). The amount of ethanol reacted per unit time, measured by the increase in the NADH extinction at a certain wavelength (for example at 340, 334 or 365 nm) is a measure of the Kallikrein activity.

Determination of Kallikrein with the aid of the substrate according to the invention is carried out analogously to the Bz-Arg OEt process in accordance with the following principle:

  (1)

-continued

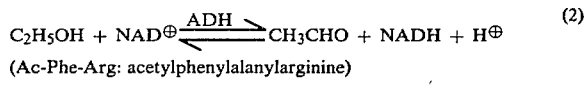

(Ac-Phe-Arg: acetylphenylalanylarginine)

The principle thus corresponds to that described by Trautschold and Werle in 1961 (benzoylarginine ethyl ester Bz-Arg OEt=BAEE as the substrate), but the sensitivity of the determination using Ac-Phe-Arg OEt is greater by a factor of 46. The non-enzymatic competing reactions (for example hydrolysis) are comparatively slight.

The reaction can be followed and recorded continuously on a spectral photometer, for example at 366 or 340 nm.

The amount of ethanol reacted according to equation (2) per unit time, measured by the increase in the NADH extinction, is a measure of the Kallikrein activity.

The amount of NADH formed according to equation (2) can be determined by the following methods:
(a) Manual process (UV test) using a spectral photometer or spectral line photometer: measurement of the NADH extinction.
(b) Determinatin in an automatic analyser: same principle as for (a).
(c) Fluorimetric process: after destroying the excess of NAD by treatment with strong alkali, the NADH formed per unit time (see equation (2)) is converted into a fluorescent product. The increase in fluorescence per unit time is a measure of the Kallikrein activity.

In addition to the above-mentioned biological-pharmacological methods, the activity can also be determined with the aid of the esterolytic splitting of Ac-Phe-Arg OEt (according to equation (1)), by the following methods known for Bz-Arg OEt:
(1) Continuous automatic microtitration of the carboxyl groups liberated (analogously to the method of Trautschold and Werle, Hoppe Seylers Z. physiol. Chem. 325, 48 (1961)).
(2) Volumetric determination of the carboxyl groups using bicarbonate /$CO_2$ buffer (analogously to the method in the literature reference immediately following equation 1)).
(3) Determination of the ester bond as a colour test (analogously to the method of S Hestrin, J. Biol, Chem 180, 249 (1949)).

The abbreviations and trademarks used in the following Examples have the following meaning:

| | |
|---|---|
| Ac-Phe-Arg OEt | = acetylphenylalanyl-arginine ethyl ester |
| L-Arg OEt . 2 HCl | = hydrochloride of L-arginine ethyl ester (= L-α-amino-δ-guanidyl-valeric acid ethyl ester) |
| CM-"Sephadex" (Trade Mark) C-25 | = a crosslinked polydextran gel substituted by carboxymethyl groups. |
| Ac-Phe-Arg | = acetyl-phenylalanyl-arginine |
| Bz-Arg OEt | = benzoylarginine ethyl ester |
| NAD | = reduced form of nicotinic acid amide-adenine dinucleotide (reduced in the pyridine part) |
| Ac-Phe-Arg OEt | = acetyl-phenylalanyl-arginine ethyl ester |
| ADH | = alcohol dehydrogenase from yeast |
| Phe | = phenylalanine |
| Arg | = arginine |
| HOAC | = acetic acid |

EXAMPLE (1) SYNTHESIS OF AC-PHE-ARG OET (a) L-Arg OEt.2 HCl is prepared by a method analogous to the preparation of the corresponding methyl ester in R.A. Boissonnas, S. Guttmann, R. L. Huguenin, P.-A. Jaquenond and E. Sandrin, Helv. Chim. Acta, 41, 1867 (1958). 30 ml of ethanol is cooled to −10° C. and 4.75 ml (65 mmols) of thionyl chloride is added in the course of 30 minutes.

After adding 10.5 g (50 mmols) of L-arginine.HCl, the mixture is kept at 45° C. under a reflux condenser for 90 minutes, while stirring and with exclusion of moisture, and then further stirred at room temperature overnight. 8.0 g (58%) of the ester precipitates and the product is recrystallised from ethanol. Melting point (uncorrected) 119–120° C. G. Weitzel, R. Renner and H. Guglielmi, Hoppe-Seyler's Z. Physiol. Chem. 352, 1617 (1971) give a melting point of 115° C. (synthesis with ethanol/HCl).

$[\alpha]^{27°}$ C.D = +11.6°±0.3° (c=2 in water)

Analysis: calculated: C 34.92%; H 7.33%; N 20.36%. found: C 34.90%; H 7.24%; N 20.70%.

According to thin layer chromatography (silica gel; running agents: n-butanol/glacial acetic acid/water 80:20:20 and n-butanol/pyridine/glacial acetic acid/water 40:10:10:20; staining with Sakaguchi reagent and with chloro-tolidine) the product is a single compound, even when 200 nmols are applied.

(b) Ac-Phe-Arg OEt.HOAC 0.829 g (4 mmols) of N-acetyl-L-phenylalanine are dissolved in 40 ml of dimethylformamide. 1.10 g (4 mmols) of finely powdered L-arginine ethyl ester dihydrochloride, 0.56 ml (4 mmols) of triethylamine and 0.69 g (6 mmols) of N-hydroxysuccinimide are added and the mixture is cooled to −15° C. After adding 0.91 g (4.4 mmols) of dicyclohexylcarbodiimide, the mixture is stirred at −5° C. for 7 hours, at 5° C. overnight and at room temperature for 5 hours. The precipitate is filtered off and the solution is concentrated almost to dryness in vacuo on a rotary evaporator. After taking up the residue in 80 ml of water, the pH of the solution is adjusted to 6.0 with triethylamine and the solution is discharged onto a column (1.5×40 cm) of Cm- "Sephadex" (Trade Mark) C-25, equilibrated with 0.05 M triethylammonium acetate of pH 6.0. Elution is carried out with a linear gradient increasing to 0.2 M triethylammonium acetate of pH 6.0 (720 ml; 50 ml/hour; size of fraction: 8 ml). Fractions 75–110, which, according to spotting on filter paper and spraying with Sakaguchi reagent, contains most of the eluted material, is lyophilised. 0.5 ml of ethanol is added to the combined residues and the product is precipitated with 60 ml of ethyl acetate. The precipitate is dried over phosphorus pentoxide in a desiccator.

Yield: 1.28 g ≙ 71%.

Melting point (uncorrected) 81–85° C.

$[\alpha]^{27°}D = -9.8°±0.3°$ (c±2 in water).

Analysis: calculated: C 55.86%; H 7.37%; N 15.51%. found: C 55.57%; H 7.58%; N 15.08%.

According to thin layer chromatography under the above conditions, the product is a single compound; after hydrolysis with bovine trypsin, only Ac-Phe-Arg can be detected. Titration with alkali metal hydroxide solution after hydrolysis of the ester with bovine trypsin: 100.2% of theory.

Aminoacid analysis after HCl hydrolysis: Phe$_1$Arg$_{0.990}$; content of aminoacids: 102.6% of theory.

Example (2) Determination of Kallikrein in human urine using Ac-Phe-Arg OEt (based on the test with Bz-Arg OEt of I. Trautschold and E. Werle, Hoppe-Seyler's Z. Physiol. Chem. 325 (1961) 48–59).

2.00 ml of buffer (0.15 M sodium pyrophosphate, 0.15 M semicarbazide hydrochloride, and 0.0375 M glycine; pH adjusted to 8.7 with sodium hydroxide solution), 0.10 ml of NAD (30 mM in water), 0.10 ml of Ac-Phe-Arg OEt (as the acetate; 15 mM in water) and 0.020 ml of ADH (alcohol dehydrogenase from yeast, Boehringer; suspension containing 100 mg/3.4 ml) are mixed in a cell of cell thickness 1 cm, thermostatically controlled at 25.0° C.

Water is added to adjust the final volume (after adding the sample) to 3.00 ml. The mixture is pre-incubated for 5 minutes. The reaction is then started by adding a 0.010 to 0.500 ml sample (solution of purified Kallikrein from human urine in water). The amount of enzyme should be chosen so that the increase in extinction in 10 minutes is between 0.05 and 0.2 extinction units. Up to the latter value, the rate of reaction is proportional to the amount of urine Kallikrein. The increase in extinction at 366 nm against a comparison cell containing water is followed for exactly 10 minutes, starting 2 minutes after the addition of the sample. A blank is run parallel, in which the urine Kallikrein sample is replaced by water. (It is sufficient to determine from 2 to 3 blank values per working day). The amount of urine Kallikrein added in U (1 U corresponds to the hydrolysis of 1 umol of Ac-Phe-Arg OEt per minute under the above conditions) is calculated from the increase in extinction of the sample measured, after substracting the blank value, with the aid of the extinction coefficient of NADH. (1 mol of ethanol, which gives 1 mol of NADH, is liberated per mol of ester hydrolysed).

What is claimed is:

1. Acetylphenylalanyl-arginine ethyl ester or an acid addition salt thereof.

2. A process for the diagnostic determination of small amounts of Kallikrein which comprises adding Kallikrein in a liquid medium to a substrate of acetylphenylalanyl-arginine ethyl ester or an acid addition salt thereof and determining the Kallikrein content therefrom by measuring liberated ethanol or carboxylic groups.

3. A process according to claim 2, in which diagnostic determination is of the Kallikrein content in urine.

4. A process according to claim 2, in which diagnostic determination is of the Kallikrein content in saliva.

5. A process according to claim 2, in which diagnostic determination is of the Kallikrein content in glands.

6. A process of claim 2 wherein the liberated ethanol is measured.

7. A process of claim 2 wherein the liberated carboxylic groups are measured.

* * * * *